United States Patent [19]

Graham

[11] 4,256,095

[45] Mar. 17, 1981

[54] ELECTROMECHANICAL THERAPEUTIC APPARATUS

[76] Inventor: David J. Graham, 18 Edithvale Ave., Willowdale, Ontario, Canada, M2N 2R5

[21] Appl. No.: 955,141

[22] Filed: Oct. 26, 1978

Related U.S. Application Data

[63] Continuation of Ser. No. 761,693, Jan. 24, 1972, abandoned.

[51] Int. Cl.³ .............................................. A61N 1/40
[52] U.S. Cl. ................................ 128/24.1; 128/24 R; 128/419 N; 128/376; 5/109
[58] Field of Search .................. 128/24 R, 24.5, 24.1, 128/1 C, 362, 1.3, 1.5, 376, 378, 419 R, 419 N, 421, 33; 5/109, 412, 61, 127; 272/86, 49

[56] References Cited

U.S. PATENT DOCUMENTS

| 399,084 | 3/1889 | Schmalz et al. | 128/376 |
|---|---|---|---|
| 1,425,743 | 8/1922 | Baruch | 128/422 |
| 2,009,270 | 7/1935 | Mayer | 128/24 R |
| 2,617,122 | 11/1952 | Chisholm | 5/109 |
| 3,013,281 | 12/1961 | Steiner | 128/24 R |
| 3,678,337 | 7/1972 | Grauvogel | 128/419 N |
| 3,750,672 | 8/1973 | von Berckheim | 128/376 |
| 3,769,641 | 11/1973 | Harper et al. | 125/109 |

FOREIGN PATENT DOCUMENTS

| 557338 | 2/1957 | Italy | 5/109 |
| 100770 | 12/1916 | United Kingdom | 128/376 |

*Primary Examiner*—Robert W. Michell
*Assistant Examiner*—Arthur S. Rose
*Attorney, Agent, or Firm*—Michael M. Sakovich

[57] ABSTRACT

Apparatus for treating a human subject in controllable gravitational and electrical fields includes a platform that is adapted to carry the body in a prostrate position. The platform is cyclically and uniformly displaced about a fixed horizontal axis by support means that are rotatably coupled to the platform and driven by a motor through a speed reducer. An AC generator is mounted under the platform and produces a low frequency signal connected across a pair of electrodes located at opposite ends of the platform. As the platform is displaced, the body is subjected to a uniformly varying gravitational field together with a low energy electrical field between the electrodes which produce in the subject a feeling of well-being and relaxation.

10 Claims, 5 Drawing Figures

ELECTROMECHANICAL THERAPEUTIC APPARATUS

BACKGROUND OF THE INVENTION

This is a continuation of application Ser. No. 761,693, filed Jan. 24, 1977, now abandoned.

This invention relates to electromechanical therapeutic apparatus, and more particularly to such apparatus for treating a human subject in controllable gravitational and electrical fields.

The prior art in respect of electrotherapeutic apparatus for treating human subjects is fraught with references that refer to high-frequency radiating equipment useful in the treatment of various disorders. This equipment, also known as diathermy apparatus, enjoys current use and produces beneficial results in treating patients having anatomical disorders that require the application of heat. The heating effect produced by the diathermy apparatus is internally generated as a result of molecular friction which occurs when a body is subjected to a high-frequency, high intensity electric field. There is, in addition, known low frequency apparatus, such as taught by U.S. Pat. No. 3,241,557, MASAKI, issued Mar. 22, 1966, which operates in a frequency range of from 10 to 200 Hertz and provides therapeutic benefits without generating internal heat.

Although the foregoing apparatus of the prior art is principally useful in the treatment of physiological disorders, its benefits extend into and affect the psychological well-being of a human being since an unstressed and rested body is conducive to a corresponding mental state. There is, however, known apparatus having a principal objective of directly influencing the psychological state of a human subject, with physiological benefits being derived as a concomittant feature. Thus, the teachings of U.S. Pat. No. 3,521,641 FARENSBACH, issued July 28, 1970, refer to apparatus that induces sleep, eases tensions, and the like in a human subject by generating a low frequency pulse train which is applied across the muscles in the region of the eyes and neck.

The utility of the aforenoted apparatus has been well documented and finds usage in current methods of therapeutic treatment. However, there are certain common recognized drawbacks that must be considered when applying such apparatus. For instance, the diathermy equipment requires close control of its output field together with length of exposure since excessive exposure can physically burn a human body. Moreover, electrical connections and body contacting electrodes are used which means there exists a possibility of shock hazard. As a result of such factors, operators generally require special training in the correct application of the apparatus. In addition, there is the problem of accidental misapplication of the equipment which could result in injury to a human subject.

SUMMARY OF THE INVENTION

An embodiment of the present invention as described herein provides apparatus which may be used to ease tensions, relieve anxiety and stress and induce an altered state of consciousness in a human subject without requiring the services of a skilled and trained operator.

The aforenoted embodiment of the present invention operates with low level gravitational and electrical fields so that overexposure does not present a problem.

The invention futher provides the generation and formation of an electric field gradient along the length of a human body with the application of only one electrode that requires physical contact, thus reducing the shock hazard.

The foregoing drawbacks of the apparatus known in the art may be substantially overcome and the provisions of the invention herein described achieved by recourse to my invention which is an electromechanical therapeutic apparatus. The apparatus comprises transport means having a supportive surface adapted to carry a reclining human body through a predetermined continuum of vertically spaced horizontal planes and further comprises support means that is rotatably coupled to the transport means for cyclically and uniformly displacing the supportive surface in a substantially horizontal planar attitude compltely around a predetermined horizontal axis and through the continuum of horizontal planes. Generator means are provided having a low voltage output producing a continuous uniformly varying low frequency signal that is free of discontinuities. In addition, electrode means are disposed at opposite ends of the transport means and are connected across the output of the generator means to produce a low energy electric field between the ends of the transport means in response to the signal.

DESCRIPTION OF THE DRAWINGS

The invention will now be more particularly described with reference to embodiments thereof shown, by way of example, in the accompanying drawings wherein.

DESCRIPTION OF THE ILLUSTRATED EMBODIMENTS

Figure 1:
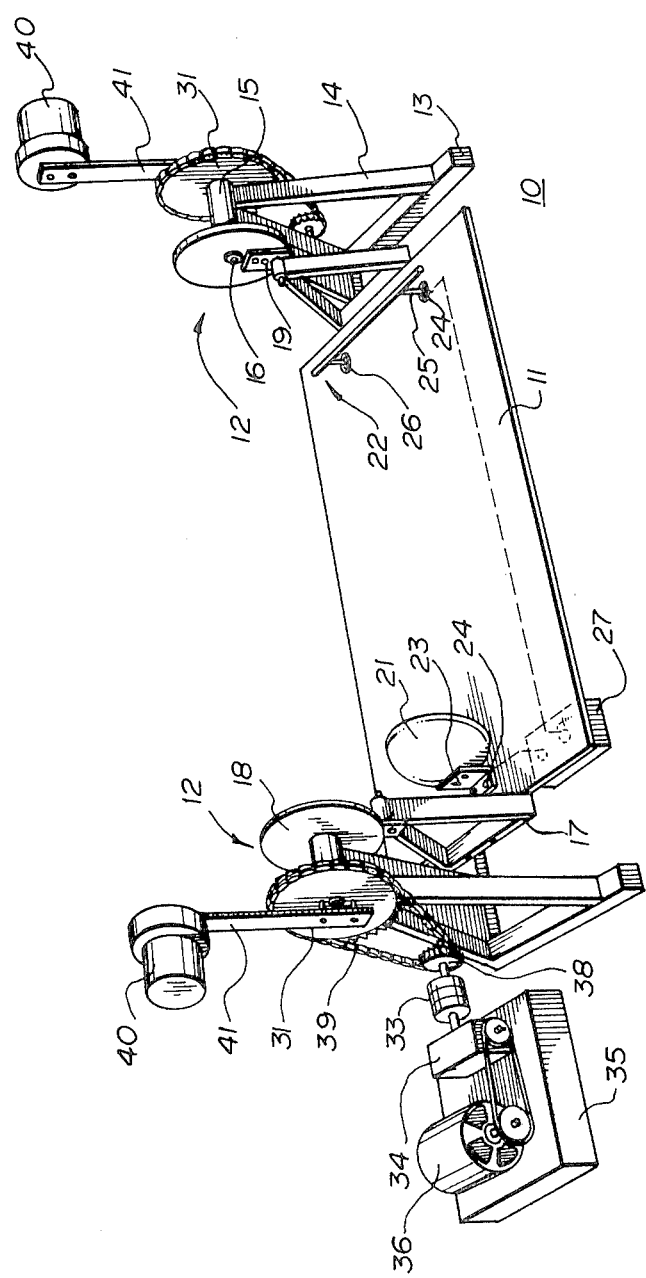
FIG. 1 is a perspective view of an embodiment of the invention.

Referring now to the drawings, FIG. 1 illustrates an elecromechanical therapeutic apparatus 10 which embodies the principles of the present invention. It will be observed that the apparatus 10 is provided with a platform 11 which is used as transport means adapted to carry a subject such as a human body in a prostrate position without tipping the body off. It will be further observed that the platform 11 has a long dimension in keeping with its intended purpose. At each end of the long dimension there are provided support means 12 which are rotatably coupled to the platform 11 for cyclically and uniformly displacing the platform about a fixed horizontal axis. This axis is not indicated in FIG. 1 in order to depict more clearly the structure of the apparatus 10. The location of such axis is specified in the description of the support means 12 herein to follow.

The drawings show that the support means 12 includes a base 13 which is in the form of a U-shaped frame having an upstanding frame member 14 mounted at each end. The upstanding portions of the member 14 come together at an apex above the base 13 and the apex is joined to a bearing housing 15 which is adapted to receive a first drive shaft 16. The shaft 16 is in turn secured to a drive plate 18 from which a hanger frame 17 is rotatably suspended via a spindle bracket 19. Each spindle bracket 19 comprises an arm having a proximate end that is fixedly secured to the output end of a shaft 16 via its drive plate 18. The distal end of each bracket 19 extends radially from the shaft 16 and carries a spindle that is disposed parallel to the shaft. As in the case of the upstanding portions of the member 14, each frame 17 has similar portions that are joined at an apex which is adapted as a bearing housing to receive the spindle portion of a bracket 19.

Figure 3:
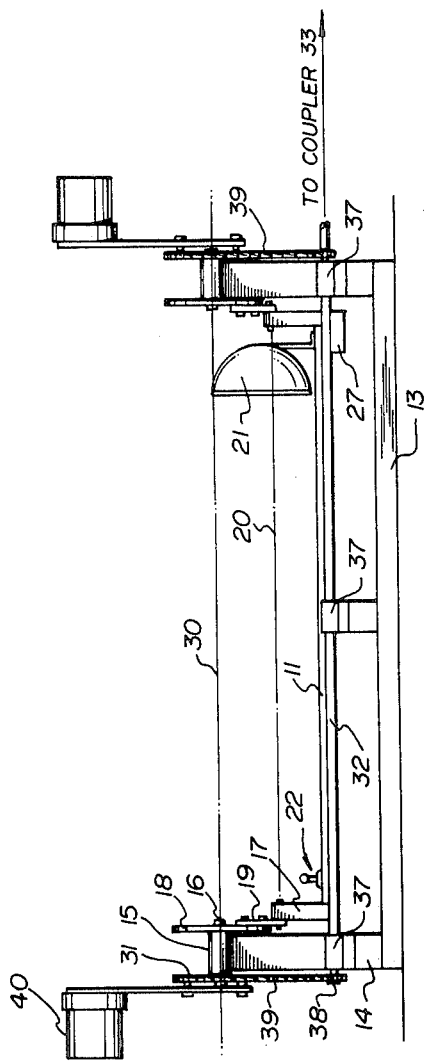
FIG. 3 is a rear elevation view of the embodiment shown in FIG. 1 and illustrates the location of a drive shaft which transmits a torque force from a motor to support means disposed at opposite ends of the apparatus.

FIGS. 1 and 3 illustrate that the platform 11 is disposed between a pair of the frames 17 and that the frames are secured to the platform 11 by conventional means such as lag screws. As appears evident in the figures, the platform 11 will rotate about a predetermined horizontal axis 20 as the shafts 16 revolve without tipping the subject off the platform 11. It will be noted in FIG. 3 that the axis 20 is substantially in alignment with the spindles of the brackets 19 when the brackets 19 are at their lowermost positions.

FIGS. 1 and 3 also show that the platform 11 carries on its uppermost surface a head electrode 21 and a foot electrode 22 for making electrical contact with the feet of the subject. Conventional means are used to mount the electrode 21 on the platform 11. Thus, the electrode 21 is secured by means of a rearwardly mounted bracket 23 and fastening screws 24. The electrode 22, on the other hand, is supported by means of a pair of posts 25 each having a flanged supporting base portion 26 which is movable on the platform 11 to accommodate subjects with bodies of different lengths.

In one corner of the lowermost surface of the platform 11 there is located an AC generator 27 having an output that is connected across the electrodes 21 and 22. It will be noted that the electrode 22 is connected to the ground side of the generator 27. The respective connections are shown in broken line form. In the embodiment illustrated, the generator 27 is of a known type and provides an output signal which is a sine wave having a voltage range of from 0.01 to 10 volts and a frequency range of from 60 to 180 Hertz.

A source of AC power for the generator 27 is not shown in the drawings. The achievement of a power connection is not a problem despite the movement of the platform 11 since the vertical and side to side travel of the platform is not great. An AC cord may therefore be conventionally connected to a source of alternating current power, leaving sufficient slack in the cord to accommodate the displacement of the generator 27 as it moves with the platform 11.

In order to obtain smooth and uniform rotation of the platform 11, the shafts 16 are aligned coaxially along a common axis 30 which is disposed in a vertical plane with the axis 20. The output end of each shaft 16 faces inwardly of the apparatus 10 in order to carry the platform 11 between the plates 18.

An input end of each shaft 16 is shown connected to a sprocket 31. It will be observed that each sprocket 31 is driven by a drive shaft 32 which is connected to a coupler 33 of a speed reducer 34. The end of the shaft 32 nearest the coupler 33 mounts a first sprocket 38 which is coupled via a drive chain 39 to the sprocket 31. In a similar manner, the end of the shaft 32 furthest from the coupler 33 is also coupled to the sprocket 31 at that end of the apparatus 10 via a second sprocket 38. Both sprockets 38 thus provide a dual drive system. FIG. 1 shows the reducer 34 mounted on a base 35 and driven by a motor 36 using a belt and pulley arrangement.

The shaft 32 is more clearly shown in FIG. 3 where, in order to provide adequate support for the shaft 32, it is rotatably journalled in three bearings 37 that stand off from the member 14. It has been found that smooth and continuous rotation of the plaform 11 is facilitated if whiplash is reduced in the shaft 32. The arrangement of bearings 37 illustrated provides a convenient means to obtain true rotation of the shaft with a minimum of whiplash. It will be understood that the term 'whiplash' refers to the radius of a circle described by a rotating shaft when the shaft is bowed and its long axis is displaced about its axis of rotation.

Optimum results are obtained with the apparatus 10 when the platform 11 is cyclically and uniformly displaced about the axis 20. In order to facilitate such movement, counterweights 40 are mounted on corresponding counterweight arms 41 which are, in turn, secured to respective ones of the sprockets 31. Each counterweight 40 may be positioned on the arm 41 in order to balance the apparatus 10 with a subject to prevent jerky or uneven movement of the platform 11. Accordingly, the inertia developed by the counterweights 40 tends to obviate jerk at the apogee and perigee of the platform 11 where motor slip is likely to occur due to the changing direction of a load comprising the platform 11 and a subject thereon. In this respect, the counterweights 40 are made adjustable to permit balancing the apparatus 10 irrespective of the weight of the individual lying on the platform 11.

It will be understood that both sprockets 31 are driven by the drive shaft 32 in order to achieve an optimum uniformity of displacement of the platform 11. The combination of a dual drive system as described together with heavy damping provided by the counterweights 40 provides the required kind of displacement.

Figure 2:
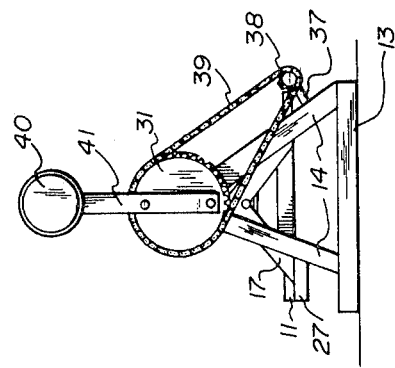
FIG. 2 is an end view of the apparatus shown in FIG. 1 with some portions being removed to more clearly show the structure.

It is clearly shown in FIG. 2 that the position of each counterweight 40 is directly opposite the platform 11 in order to balance the apparatus carrying a subject. Although not shown in the drawings, it would be apparent to those skilled in the art that balancing adjustments would be facilitated by means of a graduated scale located on each arm 41. In this way the weight of a subject may first be determined and the apparatus 10 balanced for that particular weight by adjusting the counterweights 40 in accordance with the scale.

Since the hanger frames 17 are each suspended from a single spindle, an off-balance condition arises in the event that a subject is not directly in line with the vertical plane containing the axes 20 and 30. The platform 11 therefore has a tendency to roll somewhat as it rotates about the axis 20. If excessive, this rolling condition detracts from the uniformity of movement about the axis 20 and it has been found that the beneficial effects of the apparatus 10 are diminished. Accordingly, when positioning a subject on the platform 11 care should be taken to ensure that the subject is aligned as closely as possible with the aforenoted vertical plane.

Figure 4:
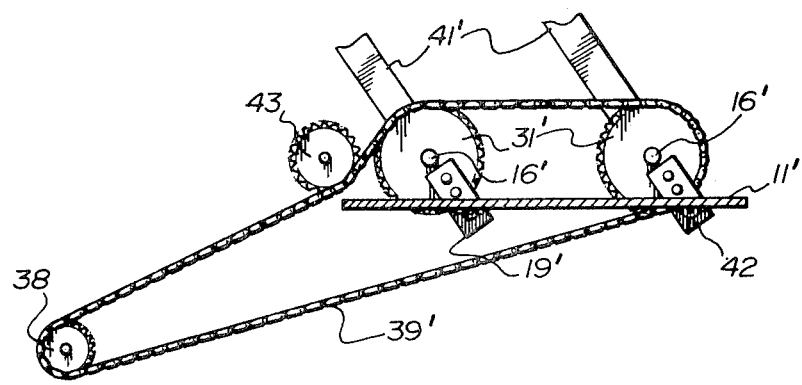
FIG. 4 is a partial end view of another embodiment of the invention.

A further embodiment of the invention is illustrated in part of FIG. 4. The entire apparatus is not shown since the basic elements are substantially the same. Although the frame structure and drive apparatus appearing in FIG. 1 are still required, it will be noted that the support means 12 has been modified to include first and second drive shafts 16' and a pair of sprockets 31' at each end of the apparatus 10. The purpose of this embodiment is to provide a structure having additional supporting to substantially eliminate roll of the platform 11' when it is supported by the spindles of the brackets 19'. Two brackets 19' are therefore required at each end of the apparatus 10, one for each sprocket 31'. In this embodiment the frames 17 are not required, the platform 11' being mounted above the spindles of the brackets 19' with each spindle being journalled in a bearing 42 that is secured to the under surface of the platform 11'. The platform 11' is thus supported by the spindles of two brackets 19' at each of its ends. This arrangement provides a more stable platform which is less critical in respect of weight distribution on its upper surface and platform roll is virtually eliminated.

The means for driving the sprockets 31 is basically the same in each of the embodiments illustrated and described. In the embodiment of FIG. 4, however, there is required an idler sprocker 43 which is adjustable in order to maintain a proper tension and increase wrap-around in the drive chain 39'.

Figure 5:
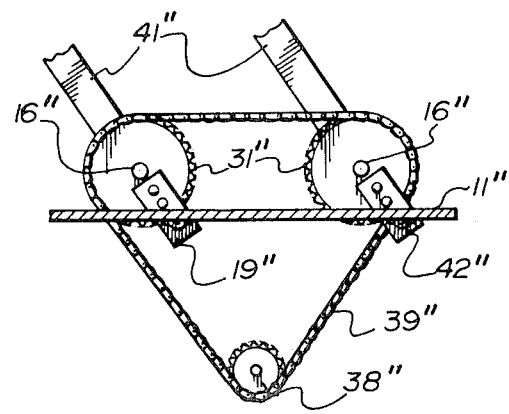
FIG. 5 is a partial end view of still another embodiment of the invention.

FIG. 5 shows an embodiment similar to that illustrated in FIG. 4. The main difference is that the sprocket 43 of FIG. 4 is not required, the correct tension in the chain 39" being obtained by adjusting the position of the sprocket 38".

In the embodiments of the invention, reference has been made to sprockets and drive chains as means for coupling torque. It will be understood by those skilled in the art that various alternate forms of torque coupling may be used. Two obvious alternatives are gear and belt drives. It will be understood therefore that the sprockets and chains shown in the figures have been indicated as such merely to provide a simplified pictorial representation and that each of the aforenoted alternatives may be used with equal facility.

As regards the various means for coupling torque, gears and drive chains are more likely to keep the two ends of the apparatus 10 synchronized. It is therefore recommended that gears and drive chains be used. Drive belts and pulleys may be substituted, but problems in synchronizing the movement of the brackets 19 will be encountered if belt slippage occurs.

Referring again to FIGS. 4 and 5, it will be understood that these figures are partial views showing the essential differences only of the three embodiments described. Accordingly, the arms 41' and 41", the end portions of which are broken away, are shown merely to indicate that dual counterweights 40 are required in order to balance the apparatus 10.

The configurations of the electrodes 21 and 22 have been found to be suitable and provide reproducible results. While other forms of electrodes may be used, a hemispherical head electrode 21 and a bar type foot electrode 22 are described since these were the forms of electrodes used during the successful development and testing of the present invention. The dimensions of the electrode 21 are not critical. Nor is either electrode critical in respect of electrically conductive material from which it is fabricated. The electrode 21 illustrated in the drawings is fabricated of copper and is in the form of a hemisphere as indicated, with a diameter that may vary from about 3 to 20 inches with a corresponding variation in depth.

Tests conducted with a number of subjects have shown conclusively that the advantages of the invention are achieved through the combination of movement of a human body through the gravitational field as disclosed together with the application of a low intensity electrical field along the length of the body when it is positioned between the electrodes 21 and 22 with the bare feet contacting the electrode 22. It has been found that the movement of the platform 11 about the axis 20 may be either circular or elliptical, the main requirement being uniformity of motion. The speed of rotation is not critical but should not be less than one revolution per minute. Good results have been obtained with rotational speeds of up to thirty revolutions per minute. The rotational speed should not be excessive, however, since if the speed becomes too great, there is a tendency for the subject to achieve a good gravity condition at the apogee of the platform 11 which detracts from uniform rotation and optimum results.

Shock hazard is virtually nonexistent since the electrode 21 is positioned over the top of the head of the subject and within six inches of the subject but does not physically touch. However, it will be understood that the bare feet of the subject are in contact with the electrode 22, preferably in the arch of each foot. Furthermore, the voltage output from the generator 27 is low, of the order of from 0.01 volts to 10 volts, which is insufficient to produce electrical shock even in the event that the subject comes in contact between both electrodes.

The generator 27 used in the embodiment of FIG. 1 produces a low frequency sine wave output with a frequency range of from 60 to 180 Hertz. Other output wave forms may be used but it is important to note that if an output signal other than a pure sine wave is used, the signal should be continuous, uniformly varying and free of discontinuities.

There are other ways of producing movement relative to gravity in other than a simple circular motion. An example is the motion of a piston in an internal combustion engine. Such alternatives may be used, but it is important to note that the motion must be continuous, uniformly varying and free of discontinuities.

The interaction of the artificially created gravitational field developed by the rotating platform 11, together with the electric field, produces in the subject a feeling of well-being and relaxation with some loss of time sense. An exposure period of about five to fifteen minutes is usually sufficient to produce both mental and physical relaxation in the subject. Longer periods of exposure may be used but do not seem to enhance the relaxation effects. It is stressed, however, that both fields are required to produce such beneficial effects. Tests in this regard have indicated that the invention will not operate in the absence of one field.

Having regard to the foregoing description and the accompanying drawings, it will be understood that in the best mode of operation of the apparatus 10, the platform 11 is adapted to carry a reclining human body through a predetermined continuum of vertically spaced horizontal planes. Such a continuum of horizontal planes occurs between the apogee and perigee of the platform 11 relative to the base 13. As the platform is carried upwardly and downwardly through the continuum by the rotating plates 18 and brackets 19, reference to FIG. 2 shows that the supportive or uppermost surface of the platform 11 is in a horizontal plane and indicates that the horizontal attitude of this plane is substantially maintained as the platform 11 traverses the vertical distance between its apogee and perigee.

It will be apparent to those skilled in the art that the preceding descriptions of embodiments of the invention may be substantially varied to meet particular specialized requirements without departing from the true spirit and scope of the invention disclosed. The embodiments described therefore are not to be taken as indicative of the limits of the invention but rather as exemplary structures of the invention which is defined by the claims appended hereto.

What I claim is:

1. Electromechanical therapeutic apparatus, comprising:
   transport means having a supportive surface adapted to carry a reclining human body through a predetermined continuum of vertically spaced horizontal planes;
   support means rotatably coupled to the transport means for cyclically and uniformly displacing the supportive surface in a substantially horizontal planar attitude completely around a predetermined horizontal axis and through the continuum of horizontal planes;
   generator means having a low voltage output producing a continuous uniformly varying low frequency signal that is free of discontinuities; and
   electrode means disposed at opposite ends of the transport means and connected across said output to produce a low energy electric field between said ends in response to said signal.

2. Apparatus as claimed in claim 1 wherein the displacing direction of said transport means includes horizontal and vertical components.

3. Apparatus as claimed in claim 2 wherein the transport means comprises a platform having a long dimension and mechanical coupling means disposed at opposite ends thereof rotatably connected to the support means.

4. Apparatus as claimed in claim 3 wherein the support means comprises:
   a base having a long dimension greater than said dimension of the platform;
   a frame member upstanding at each end of the base and fixedly secured thereto; and
   a first drive shaft rotatably journalled in each frame member, each shaft having an input end facing outwardly of the base for connection to a source of rotary power and an inwardly facing output end rotatably connected to said coupling means.

5. Apparatus as claimed in claim 4 wherein the support means further comprises:
   a drive motor secured to the base adjacent one frame member; and
   speed reducing means having an input coupled to an output shaft of the motor, and an output coupled to the input end of at least one drive shaft for rotating said coupling means.

6. Apparatus as claimed in claim 5 wherein the coupling means comprises:
   a pair of arms, each arm having a proximate end fixedly secured to the output end of one drive shaft and a distal end extending radially therefrom and carrying a spindle disposed parallel to said drive shaft; and
   a pair of hanger frames having ends, one end of each frame being rotatably connected to the spindle of an arm, and the opposite end of each frame being fixedly secured to an end of said platform.

7. Apparatus as claimed in claim 6 wherein the generator produces a sine wave output having a voltage range of from 0.01 to 10 volts.

8. Apparatus as claimed in claim 7 wherein the sine wave output has a frequency range of from 60 to 180 Hertz.

9. Apparatus as claimed in claim 8 further comprising:
   a plurality of counterweight arms, individual ones of which having a proximate end fixedly secured to the input end of a drive shaft and a distal end extending radially therefrom in a direction opposite to the distal end of said arm in the coupling means; and
   a plurality of counterweights, individual ones of which are mounted on the counterweight arms to balance said apparatus.

10. Electromechanical therapeutic apparatus, comprising in combination:
    means for cyclically and uniformly displacing a reclining human body completely around a predetermined horizontal axis and through a continuum of vertically spaced horizontal planes while maintaining the body in a substantially fixed horizontal attitude;
    generator means having a low voltage output producing a continuous uniformly varying low frequency signal that is substantially free of discontinuities; and
    electrode means connected across said output and disposed on the displacing means adjacent opposite ends of the body such that the electrode means are stationary relative to the body when the body is displaced, the electrode means producing a low energy electric field intermediate said ends in response to said signal.

* * * * *